(12) United States Patent
Dekker et al.

(10) Patent No.: US 8,034,580 B2
(45) Date of Patent: Oct. 11, 2011

(54) DETERMINING PRESENCE OF ANTIBIOTIC IN A FLUID

(75) Inventors: Angelina Dekker, Delft (NL); Comelis Jacobus Bouwknecht, Delft (NL); Johannes Theodorus Arie Van Pelt, Delft (NL); Angelique De Rijk, Ridderkerk (NL); Stark Jacobus, Rotterdam (NL); Pieter Comelis Langeveld, Delft (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 12/222,092

(22) Filed: Aug. 1, 2008

(65) Prior Publication Data

US 2008/0293093 A1    Nov. 27, 2008

Related U.S. Application Data

(62) Division of application No. 10/559,797, filed as application No. PCT/EP2004/007288 on Jul. 1, 2004, now abandoned.

(30) Foreign Application Priority Data

Jul. 2, 2003   (EP) .................................. 03077073
Nov. 24, 2003  (EP) .................................. 03078707

(51) Int. Cl.
*C12Q 1/18*    (2006.01)

(52) U.S. Cl. .......................................................... 435/32
(58) Field of Classification Search ................... 435/32, 435/34
See application file for complete search history.

(56) References Cited

U.S. PATENT DOCUMENTS

| | | | | |
|---|---|---|---|---|
| 2,967,132 | A | * | 1/1961 | Sacks .............................. 435/14 |
| 4,946,777 | A | | 8/1990 | Lameris et al. |
| 5,094,955 | A | | 3/1992 | Calandra et al. |
| 6,867,015 | B1 | | 3/2005 | Langeveld et al. |
| 2006/0134725 | A1 | * | 6/2006 | Langeveld ..................... 435/32 |

FOREIGN PATENT DOCUMENTS

| | | |
|---|---|---|
| DE | 36 13 794 | 10/1987 |
| EP | 0 005 891 | 12/1979 |
| EP | 0 418 113 A2 | 3/1991 |
| EP | 0418113 A2 * | 3/1991 |
| WO | 99/34013 | 7/1999 |

* cited by examiner

*Primary Examiner* — Ralph Gitomer
(74) *Attorney, Agent, or Firm* — Nixon & Vanderhye P.C.

(57) ABSTRACT

The pressure of an antibiotic in a fluid is determined by contacting a sample of the fluid suspected of containing an antibiotic with a test medium containing a microorganism, a substance that provides a solid state and an indicator, such as Bromothymol Blue, incubating to grow the microorganism if present in the sample and detecting growth of the microorganism indicating absence of an antibiotic or inhibition of the growth of microorganism indicating the presence of an antibiotic.

13 Claims, No Drawings

DETERMINING PRESENCE OF ANTIBIOTIC IN A FLUID

This application is a divisional of U.S. application Ser. No. 10/559,797 (now abandoned), filed Dec. 8, 2005, which in turn is the US national phase of international application PCT/EP2004/007288 filed 1 Jul. 2004 which designated the U.S. and claims benefit of EP 03077073.9, dated 2 Jul. 2003 and EP 03078707.1, dated 24 Nov. 2003, the entire content of which is hereby incorporated by reference.

FIELD OF THE INVENTION

The present invention relates to an improved novel microbiological test system and a new method for the rapid determination of the presence of antibacterial compounds in fluids such as milk, meat juice, serum and urine using said test system.

BACKGROUND OF THE INVENTION

Microbiological test methods for the determination of antibacterial compounds, particularly residues of antibiotics such as cephalosporin, penicillin, tetracycline and derivatives thereof and chemotherapeutics such as sulfa's, in fluids such as milk, meat juice, serum and urine have been known for a long time. Examples of such tests have been described in CA 2056581, DE 3613794, EP 0005891, EP 0285792, EP 0611001, GB A 1467439 and U.S. Pat. No. 4,946,777. These descriptions all deal with ready to use tests that make use of a microorganism and will give a result by the change indicated by an indicator molecule added to the test system. The principle is that when an antibacterial compound is present in the fluid in a concentration sufficient to inhibit the growth of the microorganism the color of the indicator will stay the same, while, when no inhibition occurs, the growth of the microorganism is accompanied by the formation of acid or reduced metabolites or other phenomena that will induce an indicator signal.

The test systems mentioned above include a test medium, such as an agar medium, inoculated with a microorganism, preferably a strain of *Bacillus, Escherichia coli* or *Streptococcus*, and a pH indicator and/or a redox indicator. The microorganism and the indicator are introduced into an optionally buffered agar solution, optionally nutrients are added to the solution and optionally substances to change the sensitivity to certain antimicrobial compounds are added to the solution. Finally the agar solution is allowed to solidify to form the test medium such that the microorganisms stay alive but cannot multiply because of lack of nutrients and/or low temperature. A suitable test should have the desired sensitivity with regard to the compounds to be tested for.

The problem with the test systems currently distributed on the market and/or described in literature is that they have a limited sensitivity towards certain antibiotics. One of the consequences of this problem is that for certain applications, for instance when threshold requirements are changed, an adequate test system cannot be made available with the current technology. There is thus a need for an improved test method that does not have this problem.

SUMMARY OF THE INVENTION

It is an object of the present invention to provide an improved method for the determination of antibiotics in fluids. Surprisingly, we have found that there is a positive effect attainable when applying the indicator according to the invention.

By applying the indicator of the present invention in microbiological test systems, an advantage in sensitivity towards antibiotics, such as for instance β-lactams and aminoglycosides can be achieved. By applying said indicator in a method for the determination of antibiotics in fluids, increases in sensitivity can be achieved. Said increases can amount up to 25% and even up to 100% depending on the antibiotic in question. Additionally, it has been found that the use of said indicator also results in a test system showing an improved visual contrast when comparing positive and negative samples. This latter phenomenon greatly facilitates accurate visual evaluation of test results.

The present invention provides a test system for the determination of the presence of an antibiotic in a fluid which comprises a test medium comprising a microorganism, a substance that provides a solid state and an indicator suitable for the detection of penicillin G, characterized in that said indicator is a compound having the general formula:

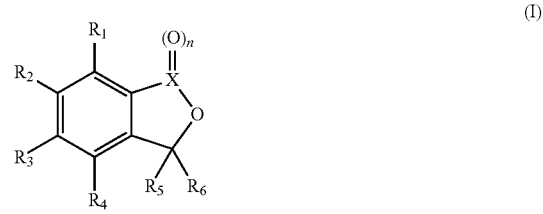

(I)

wherein $R_1$, $R_2$, $R_3$ and $R_4$ are independently of each other alkyl, halogen or hydrogen, X=C or S, n=1 if X=C and n=0, 1 or 2 if X=S, and $R_5$ and $R_6$ are independently of each other:

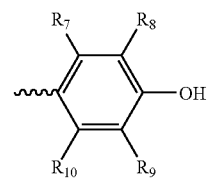

wherein $R_7$, $R_8$ and $R_9$ are, independently of each other alkyl, branched alkyl, hydrogen or halogen and $R_{10}$ is alkyl or branched alkyl, or salts thereof.

Furthermore, there is provided a method for the determination of the presence of an antibiotic in a fluid comprising the steps of:
(a) contacting a sample of said fluid with a test medium comprising a micro-organism, at least one substance that provides a solid state and an indicator;
(b) incubating the microorganism for a period of time to grow the microorganism in case no antibiotic is present in the fluid sample; and
(c) detecting growth or inhibition of growth of the microorganism with the indicator, characterized in that said indicator is a compound having the general formula (I).

Furthermore, there is provided a kit suitable for the determination of an antibiotic in a fluid comprising a container partially filled with a test medium comprising a micro-organism, a gelling agent and an indicator, characterized in that said indicator is a compound with the general formula (I).

Finally there is provided the use of a compound having the general formula (I) as indicator in a test system for an antibiotic.

DETAILED DESCRIPTION OF THE INVENTION

The terms and abbreviations given below are used throughout this disclosure and are defined as follows.

The term 'CFU' is an abbreviation of Colony Forming Units and refers to the number of microorganisms, spores of microorganisms, partially germinated spores of microorganisms or vegetative cells capable of producing colonies of microorganisms.

The term 'fluid' refers to a substance (as a liquid) tending to flow or conform to the outline of its container.

The term 'gelling agent' refers to a compound that assists in changing a mixture into or taking on the form of a gel.

The term 'indicator' refers to a substance used to measure (for example by change of color or fluorescence) the condition of a test medium with respect to the presence of a particular material (for example an acid, a base, oxidizing or reducing agents). For instance, the term 'indicator' may refer to one or more compounds that are known as pH-indicators, but also to one or more compounds that are known as redox-indicators. Also, the term 'indicator' may refer to mixtures of two or more different types of indicators, such as a combination of a pH- and a redox-indicator. In general, when two or more indicators are used, these indicators are co-operating to increase the indicator effect of each of the indicators when taken alone.

The term 'nutrient' refers to one or more nutritive substances or ingredients that promote and/or are required for the growth of microorganisms as used in the method of the present invention.

The term 'sampling device' refers to a device with the aid of which a sample of a fluid can be added to a test medium. Such a device may be a container, optionally with volume markings. Such a container may be a capillary, a syringe, a pipette or an automated pipetting system. Such a syringe or pipette may be designed in such a way that with only one mode of operation a predetermined volume can be withdrawn from the fluid to be analyzed.

The term 'sensitivity' refers to the degree of receptiveness of a given system to sense a certain state. More particularly, in the present case 'sensitivity' refers to the degree by which concentrations of antibiotics in a sample can be determined.

The term 'spore' refers to a primitive usually unicellular often environmentally resistant dormant or reproductive body produced by microorganisms and capable of development into a new individual microorganism.

The term 'test medium' refers to a composition such as a solution, a solid or, preferably, in the form of a sol or a gel, for instance comprising a gelling agent. Suitable examples of gelling agents are agar, alginic acid and salts thereof, carrageenan, gelatin, hydroxypropylguar and derivatives thereof, locust bean gum (Carob gum), processed eucheuma seaweed and the like. However, the person skilled in the art will understand that other types of solid test media may be based on carrier materials such as ceramics, cotton, glass, metal particles, paper, polymers in any shape or form, silicates, sponges, wool and the like. Usually, a test medium contains one or more indicators, however, these compounds may also be added later when the test is being performed. The test medium comprises one or more types of microorganisms as detecting agents. Optionally, the test medium may also contain one or more buffers, nutrients, stabilizers, substances that change the sensitivity to certain antimicrobial compounds in a positive or negative way, and/or viscosity-increasing agents. When a buffer is present in the medium, it may be added during the mixing of the components of the medium or the components may be dissolved and/or suspended in the buffer. Optionally the test medium is sterilized and usually the pH is adjusted to the required value. Examples of substances that change the sensitivity to certain antimicrobial compounds are antifolates like ormethoprim, tetroxoprim and trimethoprim that improve the sensitivity of the micro-organism towards sulfa compounds or salts of oxalic acid or hydrofluoric acid, which improve the sensitivity towards tetracycline. Examples of viscosity-increasing agents are is ascorbyl methylsilanol pectinate, carbomer, carboxymethyl cellulose, cetearyl alcohol, cetyl alcohol, cetyl esters, cocamide DEA, emulsifying wax, glucose, hydroxyethyl cellulose, hydroxypropylmethyl cellulose, lauramide DEA, linoleamide DEA, magnesium aluminum silicate, maltodextrins, PEG-8 distearate, polyacrylamide, polyvinyl alcohol, PVP/hexadecene copolymer, sodium chloride, sodium sulfate, soyamidopropyl betaine, xanthan gum and the like. Alternatively, the optional ingredients of the test medium mentioned above may also be added exogenously. The test medium may be contained within any type of container; frequently used containers are tubes, microtiter plates and petri dishes.

The term 'threshold' refers to the concentration value above which a given analyte is to be regarded as present and below which said analyte is to be regarded as absent. Generally, a threshold value is given for particular analytes in particular samples by local, regional or interregional authorities but it can also be pre-set for certain research purposes.

In a first aspect of the invention there is provided a test system that comprises a test medium. The test medium comprises a microorganism, a substance that provides a solid state and at least one indicator, at least one of which has the general formula (I) given above. Preferred examples of said indicator are Bromocresol Green, Bromothymol Blue, Chlorocresol Green, m-Cresol Purple, Thymol Blue and Xylenol Blue. Most preferably the indicator is Bromothymol Blue.

Preferably, the substance providing for a solid state is a gelling agent and/or a carrier material. The amount of gelling agent in the test medium is between 2 and 100 $g \cdot l^{-1}$, preferably between 5 and 50 $g \cdot l^{-1}$, more preferably between 10 and 20 $g \cdot l^{-1}$, most preferably between 12 and 15 $g \cdot l^{-1}$. Preferably the gelling agent is agar.

In an embodiment of the first aspect of the invention, the microorganism is a thermo stable microorganism such as a *Bacillus* species, preferably *Bacillus stearothermophilus*, an *Escherichia coli* species, or a *Streptococcus* species, preferably *Streptococcus thermophilus*. These species may be introduced in the test as units capable of producing colonies, or Colony Forming Units (CFU's). Said CFU's may be spores, vegetative cells or a mixture of both. The concentration of said CFU's is expressed as Colony Forming Units per ml of test medium ($CFU \cdot ml^{-1}$) and is usually in the range of $1 \times 10^5$ to $1 \times 10^{12}$ $CFU \cdot ml^{-1}$, preferably $1 \times 10^6$ to $1 \times 10^{10}$ $CFU \cdot ml^{-1}$, more preferably $2 \times 10^6$ to $1 \times 10^9$ $CFU \cdot ml^{-1}$, most preferably $5 \times 10^6$ to $1 \times 10^8$ $CFU \cdot ml^{-1}$, or still more preferably $5 \times 10^6$ to $2 \times 10^7$ $CFU \cdot ml^{-1}$.

In a second aspect of the invention, there is provided a method for the determination of an antibiotic in a fluid comprising the steps of contacting a sample of said fluid with a test medium according to the first aspect of the present invention in the presence of nutrients. Advantageously, the method provides for conditions that there is no growth of microorganism prior to the addition of fluid sample, by keeping the test medium at conditions that prevent growth, such as a relatively low temperature and/or in the absence of nutrients essential for growth. After addition of the fluid sample, growth of the microorganism is allowed to take place during a period sufficiently long for the microorganisms to grow in case no antibiotics are present, by adding nutrients, optionally before the contacting of said fluid sample, and/or raising the temperature, and/or providing for a pH-value at which the microorganism is able to grow; and detecting growth of the microorganism by observing the presence or absence of a change of an indicator. The method of the present invention also includes mixing samples (e.g. with other samples, but also with salts, buffering compounds, nutrients, stabilizers, isotope-labeled compounds, fluorescence-labeled compounds and the like), concentrating and/or diluting (e.g. with diluting liquids such as water, milk or liquids derived from milk, blood or liquids derived from blood, urine and/or solvents) samples prior to addition to the test medium.

In one embodiment of the second aspect of the present invention, the antibiotic is a β-lactam antibiotic such as a cephalosporin or a penicillin derivative. Examples of such derivatives are amoxicillin, ampicillin, cefadroxil, cefradine, ceftiofur, cephalexin, penicillin G, penicillin V and ticarcillin, but of course many other similar β-lactam derivatives are known and applicable in the method of the present invention. In another embodiment the antibiotic is an aminoglycoside such as, for instance, neomycin.

Advantageously, it was established that the method of the present invention displays selectivity with regard to antibiotics, in particular with regard to β-lactam antibiotics and aminoglycosides.

In another embodiment of the second aspect of the invention, the growth of the microorganism is to take place during a predetermined period, preferably within a time span of 0.5 to 4 hours, more preferably between 1 to 3.5 hours, most preferably between 2.0 to 3.25 hours. Preferably the growth of the microorganism is conducted at a predetermined temperature, preferably the optimal growth temperature of the micro-organism. When, for example, thermo stable microorganisms are used, said temperature preferably is between 40 and 70° C., more preferably between 50 and 65° C., most preferably between 60 and 64° C. Optionally said reaction can be carried out with the aid of a thermostatic device. Alternatively, the time required for growth of the microorganism is equal to the time that is required for a calibration sample without any analyte to induce a change in the indicator.

In still another embodiment of the second aspect of the invention, nutrients are added as a separate source, e.g. as a tablet, disc or a paper filter. Also other compounds such as the indicator(s), microorganism, stabilizers and/or antifolates may be added as a separate source, optionally incorporated in the nutrient medium.

In yet another embodiment of the second aspect of the invention, there is provided a method for determining the presence or absence of an antibiotic in a fluid sample whereby the ratio of the fluid sample to test medium exceeds 2:3 (0.68:1) (v/v). Preferably, said ratio is at least 20:27 (0.74:1) (v/v), more preferably said ratio is at least 25:27 (0.93:1) (v/v); most preferably said ratio is at least 2:1 (v/v). It has been found that there is no technical reason for an upper limit to the amount of fluid sample. In practice this volume should not exceed the maximum content of the container that holds the test medium. For example, in a 2 ml container having 0.2 ml test medium, no more than 1.8 ml of fluid sample should be added. In practice, containers for performing the method of the present invention have a volume that rarely exceeds 50 ml and hence the amount of fluid sample to be added shall not exceed 50 ml, preferably 10 ml, more preferably 5 ml, still more preferably 2 ml, most preferably 1 ml. Thus, in general, the upper limit of the ratio of the volume of fluid sample to the volume of test medium is 250:1 (v/v), preferably 50:1 (v/v), more preferably 25:1 (v/v), still more preferably 10:1 (v/v), most preferably 5:1 (v/v). Preferably, the volume of fluid sample is greater than the volume of test medium.

The result of the method of the present invention is determined by the observation of the presence or absence of a change of the indicator or indicators used. When, for example such a change is a color change, said color change may be observed visually. However in one embodiment of the invention said color change is determined using an arrangement that generates digital image data or an arrangement that generates analog image data and converts said analog image data into digital image data followed by interpretation of said digital image data by a computer processor. Such an arrangement, which may for instance be a sample-reading device such as a scanner coupled to a personal computer, is described in International Patent Application WO 03/033728, incorporated by reference, and briefly summarized below.

The arrangement can be suitably used for instance for detecting residues of antibiotics in milk. With this arrangement it is possible to scan the bottom side of each of the samples in a test plate. The color and the brightness of the reflected light are registered in three variables, each describing one color component, for instance the so-called L*a*b* model. In the L*a*b* model, the color spectrum is divided in a two-dimensional matrix. The position of a color in this matrix is registered by means of the two variables "a" and "b". The variable L indicates the intensity (for instance, from light blue to dark-blue). It is possible to male a criterion comprising the a-value, b-value and L-value to make a composite function as follows:

$$Z = w_L \cdot L + w_a \cdot a + w_b \cdot b$$

where $w_L$, $w_a$ and $w_b$ are weighting factors for the L-value, a-value and b-value, respectively. The values of these weighting factors can be calculated by means of "discriminant analysis", such that the group means show a maximum distance in relation to the spreading. By combining two or more of the color components in the L*a*b* model in a predetermined manner that depends on the type of residue and the sample, an accurate detection is possible. In practice, a certain value of Z at which a test should switch between positive and negative result is experimentally predetermined.

In a third aspect of the invention there is provided a kit for carrying out the method of the second aspect of the present invention. Such a kit comprises one or more containers filled with test medium as described in the first aspect of the invention and optionally a sampling device. The containers may be test tubes of any shape and size and from any material available, provided that observation of indicator changes is possible. Also, the containers may be wells such as those incorporated in micro-titer plates.

Said sampling device is a device with the aid of which fluid can be added to said test medium. Preferably, such a device is a container, optionally with volume markings. More preferably, such a device is a syringe, a pipette or an automated pipetting system. Such a syringe or pipette may be designed in such a fashion that with only one mode of operation a predetermined volume can be withdrawn from the fluid to be analyzed. Optionally, systems known in the art with which more than one syringe or pipette can be operated with one single handling may be applied. It is the object of the second aspect of the present invention to provide a kit that allows for simple addition of the amounts of fluid to be added according the first aspect of the invention. Optionally, said kit comprises means for sealing of said containers filled with test medium during incubation and/or an insert with instructions for use and/or a means for setting the time needed for incubation.

In one embodiment of the third aspect of the invention, said kit comprises nutrients. Preferably said nutrients are contained within a medium such as a tablet, disc or a paper filter. The advantages of providing nutrients contained within a medium are that the user can easily add them to the test medium and that the amounts can be predetermined so as to avoid errors in dosing the required amounts. Also other compounds such as the indicator(s), stabilizers and/or antifolates may be added as a separate source, optionally incorporated in the nutrient medium.

In another embodiment of the third aspect of the present invention, said kit comprises a thermostatic device, with the aid of which test samples can be kept at a pre-set temperature, such as the temperature at which the microorganism shows sufficient growth. Preferably, said thermostatic device is designed in such a fashion that it can hold said containers filled with test medium. Optionally the thermostatic device is coupled to a means for setting the time needed for incubation such that heating and/or cooling is stopped after lapse of a pre-set period.

In yet another embodiment of the third aspect of the invention, said kit comprises a data carrier loaded with a computer program suitable for instructing a computer to analyze digital data obtained from a sample-reading device. Said data carrier may be any carrier suitable for storing digital information such as a CD-ROM, a diskette, a DVD, a memory stick, a magnetic tape or the like. Advantageously, said data carrier loaded with a computer program provides for easy access to the latest available computer programs suitable for use in the method of the present invention.

In a fourth aspect of the present invention there is provided the use of a compound having the general formula (I) to improve the sensitivity for an antibiotic in a microbial inhibition test.

EXAMPLES

Example 1

Comparison of Bromothymol Blue and Bromocresol Purple in Penicillin G Determination Commercially available Delvotest® MCS, prepared according to the methods described in EP 0005891, was adapted by the replacement of the indicator Bromocresol Purple by Bromothymol Blue (160 mg·l$^{-1}$). The sensitivity for penicillin G was determined by investigating samples containing different concentrations of penicillin G in different test systems. The results are summarized in the Table below (sensitivity values in ppb).

|  | Bromocresol Purple | Bromothymol Blue |
|---|---|---|
| Penicillin G[1] | 4 | 2 |
| Penicillin G[2] | 3 | 2 |

[1] Penicillin G concentrations of 0, 2, 4 and 6 ppb were investigated
[2] Penicillin G concentrations of 0, 1, 2, 3 and 4 ppb were investigated Example 2

Comparison of Bromothymol Blue and Bromocresol Purple in Determination of Various Antibiotics Commercially available Delvotest® MCS, prepared according to the methods described in EP 0005891, was adapted by the replacement of the indicator Bromocresol Purple by Bromothymol Blue (160 mg·l$^{-1}$). The sensitivity for different antibiotics was determined by investigating two sets of six experiments using either a plate test or a tube test system. The sensitivity was determined by reading the test at the moment at which an antibiotic-free control changed color. From the results as summarized in the Table below (sensitivity values in ppb), it can be seen that Bromothymol Blue gives superior sensitivities in comparison with Bromocresol purple (BP) for all antibiotics investigated with the exception of sulfadiazine in which case the results for the two indicators are identical.

|  | BP[1] | Bromothymol Blue Type of test | | | | | | | | | | | |
|---|---|---|---|---|---|---|---|---|---|---|---|---|---|
|  |  | Plate test | | | | | | Tube test | | | | | |
|  |  | Experiment # | | | | | | | | | | | |
|  | 0 | 1 | 2 | 3 | 4 | 5 | 6 | 7 | 8 | 9 | 10 | 11 | 12 |
| Penicillin G | 3 | 1 | 2 | 1 | 1 | 1-2 | 1 | 2 | 2 | 2 | 2 | 2 | 2 |
| Ampicillin | 8 | 2 | 2 | 2 | 2 | 2 | 2 | 2 | 2 | 2 | 2 | 2 | 2 |
| Amoxicillin | 8 | 4 | 2 | 2 | 2 | 2-4 | 2 | 4 | 4 | 4 | 4 | 4 | 4 |
| Cephapirin | 8 | 2 | 2 | 4 | 6 | 2 | 4-6 | 4 | 4 | 4 | 4 | 4 | 4 |
| Cloxacillin | 40 | 10 | 10 | 10 | 10 | 10 | 10 | 20 | 20 | 20 | 20 | 20 | 20 |
| Neomycin | 600 | 100 | 100 | 100 | 100 | 100 | 100 | 200 | 200 | 200 | 200 | 200 | 200 |
| Sulfadiazine | 50 | 50 | 50 | 50 | 50 | 50 | 50 | 50 | 50 | 50 | 50 | 50 | 50 |

[1] BP: Bromocresol Purple

Example 3

Concentration Effect in the Comparison of Bromothymol Blue and Bromocresol Purple Two test systems were prepared. The first system differs only from a commercially available Delvotest® MCS in that the concentration of Bromocresol Purple is 160 mg·l$^{-1}$, and the second series is as the first with Bromocresol Purple replaced with Bromothymol Blue (160 mg·l$^{-1}$). The sensitivity for penicillin G was determined reading the test at the moment at which an antibiotic-free control changed color. From the results as shown in the Table below (sensitivity values in ppb) it can be seen that the sensitivity of Bromothymol Blue is better then that of Bromocresol Purple at the same concentrations of indicator.

|  | Bromocresol Purple (160 mg · l$^{-1}$) | Bromothymol Blue (160 mg · l$^{-1}$) |
|---|---|---|
| Penicillin G | 3 | 2 |

Example 4

Comparison of Bromothymol Blue and Bromocresol Purple in Production Scale Microbiological Inhibition Test Two series of test systems were prepared on production scale. The first series is a commercially available Delvotest® MCS and the second series is as the first with Bromocresol Purple replaced with Bromothymol Blue (160 mg·l$^{-1}$). The sensitivity for different antibiotics was determined reading the test at the moment at which an antibiotic-free control changed color. The results are in the Table below (sensitivity values in ppb).

|  | Bromocresol Purple | Bromothymol Blue |
|---|---|---|
| Penicillin G[1] | 3 | 2 |
| Penicillin G[2] | 3 | 2 |
| Ampicillin[2] | 6 | 2 |
| Amoxicillin[2] | 8 | 4 |
| Cephapirin[2] | 8 | 4 |
| Cloxacillin[2] | 40 | 20 |
| Neomycin[2] | 400 | 200 |

[1]Batch #1, immediately after production
[2]Batch #1, three weeks after production

The invention claimed is:

1. A method for determining a presence of an antibiotic in a fluid, the method comprising the steps of:
   a) contacting a sample of said fluid with a test medium comprising a microorganism, at least one solid state support and Bromothymol Blue as an indicator;
   (b) incubating the test medium for 1 to 3.5 hours; and
   (c) detecting growth or inhibition of growth of the microorganism with the indicator by observing presence or absence of a change in color of the Bromothymol blue in the incubated test medium, thereby
   (d) determining the absence or presence of the antibiotic in the fluid.

2. A method according to claim 1 wherein the antibiotic to be determined is selected from the group consisting of a β-lactam antibiotic and an aminoglycoside.

3. A method according to claim 1 wherein the fluid in which the antibiotic is to be determined is a fluid obtainable from an animal or human body.

4. A method according to claim 1 wherein the ratio of the volume of said fluid to the volume of test medium exceeds 0.68:1.

5. A method according to claim 1, wherein the ratio of the volume of liquid sample to the volume of test medium exceeds 20:27 (0.74:1) (v/v), 25:27 (0.93:1) (v/v) or 2:1 (v/v).

6. A method according to claim 1, wherein the volume of liquid sample is greater than the volume of test medium.

7. A method according to claim 1, wherein the solid state support is selected from the group consisting of a gelling agent and a carrier material.

8. A method according to claim 1, wherein the test medium further comprises at least one compound selected from the group consisting of a buffer, a nutrient, a stabilizer, a substance that changes the sensitivity to antimicrobial compounds in a positive or negative way and a viscosity increasing agent.

9. A method according to claim 1, wherein the microorganism is a thermo stable microorganism.

10. A method according to claim 1, wherein the antibiotic is a β-lactam antibiotic.

11. A method according to claim 1, wherein incubating the test medium occurs for a period of time between 2.0 and 3.25 hours.

12. A method for determining a presence of a β-lactam or an aminoglycoside antibiotic in a fluid, the method comprising the steps of:
   (a) contacting a sample of the fluid with a test medium comprising a thermostable microorganism, a solid gelling agent, a solid carrier material or both and Bromothymol Blue as an indicator;
   (b) incubating the test medium for 1 to 3.5 hours; and
   (c) detecting growth or inhibition of growth of the microorganism with the indicator by observing presence or absence of a change in color of the Bromothymol Blue in the incubated test medium, thereby
   (d) determining the absence or presence of the antibiotic in the fluid.

13. A method according to claim 12, wherein incubating the test medium occurs for a period of time between 2.0 and 3.25 hours.

* * * * *